(12) United States Patent
Potyrailo et al.

(10) Patent No.: US 6,576,911 B1
(45) Date of Patent: Jun. 10, 2003

(54) METHOD AND APPARATUS FOR NONDESTRUCTIVE DETERMINATION OF POLYMER HYDROLYTIC STABILITY

(75) Inventors: Radislav Alexandrovich Potyrailo, Niskayuna; Patrick Joseph McCloskey, Watervliet; Timothy Brydon Burnell, Schenectady, all of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/690,478

(22) Filed: Oct. 19, 2000

(51) Int. Cl.[7] .................................................. B05D 5/12
(52) U.S. Cl. ................................. 250/458.1; 250/459.1
(58) Field of Search ........................ 250/458.1, 459.1; 427/8, 387; 522/99, 100; 436/60

(56) References Cited

U.S. PATENT DOCUMENTS

| | | | |
|---|---|---|---|
| 4,348,500 A | | 9/1982 | Robeson et al. |
| 4,436,879 A | | 3/1984 | Miller et al. |
| 4,474,937 A | | 10/1984 | Bales |
| 4,556,698 A | | 12/1985 | Braksmayer |
| 4,595,404 A | | 6/1986 | Kawakami et al. |
| 4,680,370 A | | 7/1987 | Williams |
| 4,802,762 A | | 2/1989 | Hill, Jr. |
| 5,047,444 A | * | 9/1991 | DeVoe et al. .................. 522/99 |
| 5,556,663 A | * | 9/1996 | Chang et al. ................... 427/8 |
| 6,127,185 A | * | 10/2000 | Melton et al. ................. 436/60 |
| 6,489,373 B2 | | 12/2002 | Kodama et al. |

FOREIGN PATENT DOCUMENTS

| | | |
|---|---|---|
| JP | 08188707 | 7/1996 |
| JP | 08208829 | 8/1996 |
| JP | 08245782 | 9/1996 |

OTHER PUBLICATIONS

Allen, N.S. et al., "Analysis of Polymer Systems by Luminescence Spectroscopy," In Chapter 4, *Analysis of Polymer Systems*, Applied Science Publishers, Ltd., London (1982).

Allen, N.S. et al., "Luminescence Applications in Commercial Polymers," *Chemistry and Industry*, vol. 2, pp. 907–913 (1978).

Allen, N.S. et al., "The Use of Luminescence Spectroscopy in Aiding the Identification of Commercial Polymers," *Analyst*, vol. 101, pp. 260–264 (1976).

Bair, H.E. et al., "Hydrolysis of Polycarbonate to Yield BPA," *J. Appl. Polym. Sci.* 26(6):1777–1786 (1981).

Chapalkatti, M.H., et al., "Investigation of Polycarbonate Degradation by Fluorescence Spectroscopy and Its Impact on Final Performance," In *Structure–Property Relations in Polymers, Spectroscopy and Performance*, Amer. Chem. Society, Ch. 25, pp. 623–642 (1993).

Gachkovskii, V.F., "Some Fluorescence Methods For Estimation of the Molecular Weights of Polymers," *Poly. Sci.* (USSR) 2199 (1965).

Golovoy, A et al., "Water Sorption and Hydrolytic Stability of Polycarbonates," *Poly. Eng. Sci.*, 29(24): 1733–1737 (1989).

(List continued on next page.)

*Primary Examiner*—Constantine Hannaher
*Assistant Examiner*—Otilia Gabor
(74) *Attorney, Agent, or Firm*—Jeffrey S. Bernard; Dougherty, Clements & Hofer (57) ABSTRACT

In an embodiment, the present invention is directed a method and an apparatus comprising irradiating a polymer sample with at least one wavelength of substantially monochromatic light and monitoring radiation emitted by the polymer sample which is correlated to sample hydrolysis and a change in polymer molecular weight.

48 Claims, 6 Drawing Sheets

OTHER PUBLICATIONS

Hoyle, C.E., et al., "Solvent Effect on the Photophysics of Bisphenol–A–Based Polycarbonate and Diphenylcarbonate," *Can. J. Chem.*, vol. 73, pp. 2062–2068. (1995).

Hoyle, C.E., et al., "Photochemistry of Bisphenol–A Based Polycarbonate: The Effect of the Matrix and Early Detection of Photo–Fries Product Formation," *J. Polym. Sci. A: Polym. Chem.*; vol. 30, pp. 1525–1533 (1992).

Humphrey, J.S., et al., "Flash Photochemical Studies of Polycarbonate and Related Model Compounds, Photodegradation vs. Photo–Fries Rearrangement," *Macromolecules* 6:305–314 (1973).

Ingle, J.D. et al., In *Spectrochemical Analysis*, Prentice Hall, Englewood Cliffs, NJ 13:376–386 and 15:460 (1988).

Knauss, D.M. et al., "Copolycarbonates Containing Hydrolytically Stable Phosphine Oxide Comonomers," *Polym. Mater. Sci. Eng.* 71:229–230 (1994).

Knauss, D.M. et al., "Polycarbonate–polydimethyl Siloxane Segmented Copolymers With Improved Hydrolytic Stability," *Polym. Mater. Sci. Eng.*, 72:232–233 (1995).

Pankasem, S. et al., Photochemistry and Photodegraduation of Polycarbonate, *Macromolecules*; vol. 27, pp. 3773–3781 (1994).

Pryde, C.A. et al., "Solid State Hydrolysis of Bisphenol–A Polycarbonate Pt.1 Effect of Phenolic End Groups," *J. Appl. Poly. Sci.*, 25(11):2573–2587 (1980).

Pryde, C.A. et al., "The Hydrolytic Stability of Some Commercially Available Polycarbonates," *Polym. Eng. Sci.* 22(6):370–375 (1982).

Rufus, I.B., et al., Identification of Fluorescent Products Produced By the Thermal Treatment of Bisphenol–A–Based Polycarbonate, *J. Appl. Polym., Sci.*; vol. 51, pp. 1549–1558.(1994).

Schollenberger, C.S., et al., "Thermoplastic Polyurethane Hydrolysis Stability," *Angew. Makromol. Chem.* 29–30:413–30 (1973).

Shah, H. et al., Photochemistry of Bisphenol–A–Based Polycarbonate: Early Detection of Photoproducts by Fluorescence Spectroscopy, *Macromolecules*, vol. 27, pp. 553–561 (1994).

Itagaki H. et al.; "Photophysical Studies of Amorphous Solids of Bisphenol A Polycarbonate", Polymer, Elsevier Science Publishers B.V, GB vol. 36, No. 1, 1995, pp. 29–34, XP004026008.

Chipalkatti, M.H. et al., "The Investigation of Thermal Degradation in Polymers by Fluorescence Spectroscopy and Potential Applications in Processing", Journal of the Americal Oil Chemists' Society, Americal Oil Chemist's Society Champaign, JS, vol. 64, Apr. 15, 1991, pp. 131–132.

Hoyle, C.E. et al., "Photochemistry of Bisphenol–A Based Polycarbonate: The Effect of the Matrix and Early Detection of Photo–Fries Product Formation", Journal of Polymer Science, Polymer Chemistry Edition, John Wiley and Sons, NY, US, vol. 30, No. 8, Jul. 1992, pp. 1525–1533.

Shah, H. et al., "Photochemistry of Bisphenol–A–Based Polycarbonate: Early Detection of Photoproducts by Fluorescence Spectroscopy", Macromolecules, American Chemical Society, Easton, US, vol. 27, No. 2, Jan. 17, 1994, pp. 553–561, XP000978609.

Pankasem, S. et al., "Photochemistry and Photodegradation of Polycarbonate", Macromolecules, American Chemical Society, Easton, US, vol. 27, 1994, pp. 3773–3781, XP0000457207.

Furus, I.B. et al., "Identification of Fluorescent Products Produced by the Thermal Treatment of Bisphenol–A–Based Polycarbonate", Journal of Applied Polymer Science, John Wiley and Sons Inc., New York, US, vol. 51, No. 9, Feb. 28, 1994, pp. 1549–1558, XP0000464426.

* cited by examiner

METHOD AND APPARATUS FOR NONDESTRUCTIVE DETERMINATION OF POLYMER HYDROLYTIC STABILITY

BACKGROUND OF THE INVENTION

The present invention is directed to a method and apparatus for high-throughput, nondestructive measurement of hydrolytic stability of polymers. The invention is particularly advantageous as a method and apparatus for fluorescent measurement of degradation of polymer molecular weight.

One important consideration in the area of polymer chemistry is long-term stability. For example, thermal variation, sunlight and hydration can cause crazes and cracks in polymers with a resulting decrease in structural integrity. Generally, two types of aging occur: physical aging and chemical aging. Physical aging often occurs as a result of the formation of water pockets in a polymer, and is associated with crack formation, voids and loss of ductility leading to premature mechanical failure (Golovoy, A. and M. Zimbo, *Polym. Eng. Sci.*, 29:1733–37 (1989)). Chemical aging occurs as a result of hydrolysis of the polymer chain, and is associated with a reduction in polymer molecular weight (Pryde, C. A. and M. Y. Hellman, *J. Appl. Polym. Sci.*, 25:2573–87 (1980); Golovoy, A. and M. Zimbo, (1989); and Knauss et al., *Polym. Mater. Sci. Eng.*, 72:232–233 (1995)).

Studies of hydrolytic degradation of polycarbonates indicate that while initial rates appear to be governed by first order reaction kinetics, over time there may be an autocatalytic effect due to an increase in phenolic end groups as the polymer degrades (Golovoy, A. and M. Zimbo (1989); Bair, H. E., et al., *J. Appl. Polym. Sci.*, 26:1777–86 (1981)). Thus, an important factor with respect to hydrolytic stability of solid polycarbonates is the degree of end-group capping. Capping of phenolic end groups by chain terminating agents minimizes the polar group content of the polymer and thereby increases hydrolytic stability (Pryde, C. A. and M. Y. Hellman, (1980)).

Also, additives may increase the rate of hydrolysis. It has been shown that chain hydrolysis is increased by base, acid, polar compounds and even by neutral species present in polymers (Golovoy, A. and M. Zimbo (1989); Pryde et al., *Polym. Eng. Sci.*, 22:370–75 (1982)). For example, brominated polycarbonate flame retardant accelerates hydrolysis (Golovoy, A. and M. Zimbo (1989)). In contrast, the hydrolytic stability of copolyester-carbonates is improved by the addition of additives (U.S. Pat. No. 4,436,879), and the hydrolytic stability of polyurethanes is improved upon addition of carbodiimide (Schollenberger, C. S. and Stewart, F. D., *Angew. Makromol. Chem.*, (1973) 29–30, 413–30). Hydrolytic stability of polymers may also be improved by the character of the polymer blend. Incorporation of phosphorous compounds into a polymer backbone may increase or decrease hydrolytic stability. For example, incorporation of phosphorous as random copolymers of polycarbonate and bis(4-hydroxyphenyl)phenylphosphine oxide (Knauss, D. M., et al., *Polym. Mater. Sci. Eng.*, 71:229–30 (1994)), or as polycarbonate formed by the reaction of aromatic trihydroxyphosphorous compounds (U.S. Pat. No. 4,680,370), or by condensation with bishydroxyalkylphosphine oxide (U.S. Pat. No. 4,556,698) is associated with increased hydrolytic stability. In contrast, phosphorous-modified polyestercarbonate resins display decreased hydrolytic stability (U.S. Pat. No. 4,474,937).

There are few methods available to evaluate the stability of polymers to chain hydrolysis. Outdoor weathering data is useful, but requires multi-year exposure times. Autoclaving samples provides for accelerated weathering. Still, because of physical changes that occur at temperatures much above 100° C., autoclave tests cannot by themselves be used to predict long-term hydrolytic stability.

Conventional techniques to determine the extent of hydrolytic degradation of a polymer involve dissolution of the sample and molecular weight determination by gel permeation chromatography (GPC). There are, however, significant drawbacks associated with this approach. The method is destructive, in that it requires the sample be dissolved, and therefore is inappropriate for field (in situ) studies of polymer integrity. Also, the method is time-consuming to perform and generates non-biodegradable waste.

Other methods to monitor polycarbonate integrity include characterization of sample "hazing" and ductility. Hazing refers to the tendency of worn polycarbonate samples to become refractive to visual light. Hazing is typically evaluated by measuring light transmittance through a sample (see e.g. U.S. Pat. No. 4,436,879). The use of hazing for analysis of polymer hydrolysis is limited in that it is difficult to establish quantitative correlation between the amount of hazing and a loss of polymer chain length or molecular weight in the presence of variations in sample thickness (flatness). Variations in sample thickness increase the error in transmission measurements of haze or other optical properties (see e.g. Ingle, J. D, and S. R. Crouch, *Spectrochemical Analysis*, Prentice Hall, Englewood Cliffs, N.J. (1988); thus, for haze measurements sample thickness should be controlled (U.S. Pat. No. 4,436,879). Also, samples must be thin enough to enable efficient and measurable transmission of light through the sample. Generally, polymers characterized by a high light transmittance exhibit improved clarity and high levels of hydrolytic stability. Conversely, polymers with poor light transmittance exhibit poor clarity and poor hydrolytic stability (U.S. Pat. No. 4,436,879). Thus, samples with decreasing yellow color, as measured by hazing, tend to exhibit increased hydrolytic stability (see e.g. JP08188707; JP08245782; and JP08208829).

Ductility refers to the relative pliability of a polymer sample. Loss of ductility is typically measured by a pellet gun impact test. Because of its destructive nature, the pellet gun test is of little use for in situ evaluation (field tests) of polymer aging. In addition, a loss of ductility as measured by the pellet gun impact test is not necessarily correlated to hydrolytic degradation or a decrease in polymer molecular weight.

Poor hydrolytic stability results in other limitations on the mechanical properties of polymers exposed to a hydrolytic environment for extended time. For example, poor hydrolytic stability may lead to a decrease in reduced viscosity of the polymer upon exposure to a hydrolytic environment (U.S. Pat. No. 4,595,404). Tests applied to evaluate mechanical properties related to hydrolytic stability include tensile modulus, tensile strength, elongation, notched Izod impact strength, viscosity and others (see e.g. U.S. Pat. Nos. 4,348,500 and 4,595,404). Still, many of these mechanical tests are destructive.

Thus, there is a need for a test which enables the nondestructive measurement of the hydrolytic stability of polymers. The test should be sensitive and capable of measurements of samples of different geometries and thickness, such that samples are not limited only to flat sections commonly used for transmission measurements. Also, the test should provide a reliable assessment of polymer molecular weight.

Preferably, such a test would enable noninvasive, high-throughput testing of samples in the field, as well as the rapid analysis of multiple laboratory samples, as for example, in a combinatorial library.

SUMMARY

The present invention is directed to a method and apparatus for rapid, high-throughput, nondestructive determination of hydrolytic stability of polymers. In one aspect, the invention comprises a method for the nondestructive determination of hydrolytic stability of polymers comprising irradiating a polymer sample with light of at least one substantially monochromatic excitation wavelength, wherein the excitation wavelengths used for irradiation are selected based upon an analysis of multiple emission spectra of the polymer irradiated at multiple excitation wavelengths; collecting fluorescent radiation emitted by the irradiated polymer sample for each excitation wavelength; monitoring emitted radiation which is substantially dependent upon polymer molecular weight; comparing the monitored radiation emitted by the polymer sample with the monitored radiation emitted from a similarly irradiated control polymer known to be substantially free of hydrolytic cleavage; and correlating a decrease of the emitted radiation substantially dependent upon molecular weight to hydrolysis of the polymer sample.

Another aspect of the invention comprises an apparatus for the nondestructive monitoring of polymer hydrolysis comprising a light source which irradiates a polymer sample with at least one wavelength of substantially monochromatic light; a probe which transmits light from the light source to irradiate the polymer sample and collects fluorescent light emitted from the sample; and a detector, wherein the detector monitors radiation emitted by the sample comprising fluorescence substantially dependent upon polymer molecular weight. Also included in the present invention are systems for performing the methods of the invention.

The methods and apparatus of the invention are noninvasive and, thus, suitable for tests of hydrolytic degradation of polymer samples which are components of a larger structure, or for combinatorial libraries in which multiple samples are arranged in an array format.

BRIEF DESCRIPTION OF THE DRAWINGS

Various features, aspects, and advantages of the present invention will become more apparent with reference to the following description, appended claims, and accompanying drawings, wherein:

DETAILED DESCRIPTION

Terms used herein are employed in their accepted sense or are defined. In this context, the present invention is directed to a method and apparatus for rapid, high-throughput, nondestructive determination of polymer degradation due to hydrolysis of the polymer chain.

In one aspect, the invention comprises a method for the nondestructive determination of hydrolytic stability of polymers comprising irradiating a polymer sample with light of at least one substantially monochromatic excitation wavelength, wherein the excitation wavelengths used for irradiation are selected based upon an analysis of multiple emission spectra of the polymer irradiated at multiple excitation wavelengths; collecting fluorescent radiation emitted by the irradiated polymer sample for each excitation wavelength; monitoring emitted radiation which is substantially dependent upon polymer molecular weight; comparing the monitored radiation emitted by the polymer sample with the monitored radiation emitted from a similarly irradiated control polymer known to be substantially free of hydrolytic cleavage; and correlating a decrease of the emitted radiation substantially dependent upon molecular weight to hydrolysis of the polymer sample. More preferably, the method further comprises applying a predetermined selection test to determine whether the sample exhibits a desired resistance to hydrolysis-induced degradation. Also more preferably, the method further comprises calculation of the useful lifetime of the polymer sample.

In an embodiment, the emitted radiation substantially dependent upon molecular weight is scaled relative to the emitted radiation which is substantially independent of sample hydrolysis. Preferably, the emitted radiation which is substantially independent of molecular weight is due to Fries product.

In an embodiment, the irradiating light comprises at least one substantially monochromatic wavelength in the range of about 200 to 550 NM. More preferably, the irradiating light comprises at least one substantially monochromatic wavelength in the range of about 270 to 350 NM. More preferably, the irradiating light comprises at least one substantially monochromatic wavelength in the range of about 290 to 330 NM. More preferably, the irradiating light comprises at least one substantially monochromatic wavelength in the range of about 300 to 320 NM. Even more preferably, the irradiating light comprises a wavelength of about 310.

In an embodiment, the wavelength of the monitored radiation comprises a range from about 200 to 900 NM. More preferably, the wavelength of the monitored radiation comprises a range from about 310 to 600 NM. In an embodiment, the wavelength of the emitted radiation substantially dependent on molecular weight comprises a wavelength in the range of about 360 to 420 NM. More preferably, the wavelength of the emitted radiation substantially dependent on molecular weight comprises a wavelength of about 380 NM. Also more preferably, the emitted radiation substantially independent of polymer hydrolysis has a wavelength of about 500 NM.

Preferably, the polymer comprises aromatic hydroxyl groups. More preferably, the polymer comprises melt polycarbonate although other types of polycarbonate may be evaluated using the method of the invention.

In another aspect, the invention comprises a method for the nondestructive determination of hydrolytic stability of polymers comprising irradiating a polymer sample with light of at least one substantially monochromatic excitation wavelength wherein the excitation wavelengths used for irradiation are selected based upon an analysis of multiple emission spectra of the polymer irradiated at multiple excitation wavelengths; monitoring fluorescent light emitted by the irradiated polymer sample at each excitation wavelength; defining at least one wavelength comprising emitted fluorescence which is substantially dependent upon molecular weight; defining at least one wavelength comprising emitted fluorescence which is substantially independent of molecular weight; scaling fluorescence which is substantially dependent upon polymer molecular weight relative to fluorescence which is substantially independent of sample molecular weight; and correlating the scaled fluorescence to sample hydrolysis. More preferably, the method further comprises applying a predetermined selection test to the scaled fluorescence to determine whether the sample exhibits a desired resistance to hydrolysis-induced degradation. Also more preferably, the method further comprises calculating the useful lifetime for the polymer sample.

Preferably, the polymer comprises aromatic hydroxyl groups. More preferably, the polymer comprises melt polycarbonate, although other types of polycarbonate may be analyzed using the method of the invention. Also more preferably, the fluorescence substantially independent of polymer molecular weight comprises fluorescence due to Fries product.

In an embodiment, the irradiating light comprises at least one substantially monochromatic wavelength in the range of about 200 to 550 NM. More preferably, the irradiating light comprises at least one substantially monochromatic wavelength in the range of about 270 to 350 NM. More preferably, the irradiating light comprises at least one substantially monochromatic wavelength in the range of about 290 to 330 NM. More preferably, the irradiating light comprises at least one substantially monochromatic wavelength in the range of about 300 to 320 NM. Even more preferably, the irradiating light comprises a wavelength of about 310.

In an embodiment, the wavelength of the monitored radiation comprises a range from about 200 to 900 NM. More preferably, the wavelength of the monitored radiation comprises a range from about 310 to 600 NM. In an embodiment, the wavelength of radiation substantially dependent on molecular weight comprises a range from about 360 to 420 NM. More preferably, the wavelength of fluorescence substantially dependent on molecular weight comprises a wavelength of about 380 NM. More preferably, the wavelength of fluorescence substantially independent of polymer hydrolysis has a wavelength of about 500 NM.

In yet another aspect, the invention comprises computer readable media comprising software code for performing the methods of the invention.

Another aspect of the invention comprises an apparatus for the nondestructive monitoring of polymer hydrolysis comprising a light source for irradiation of a polymer sample with at least one wavelength of substantially monochromatic light, a probe, wherein the probe transmits light from the light source to irradiate the polymer sample and collects fluorescent light emitted from the sample; and a detector, wherein the detector monitors radiation emitted by the sample comprising fluorescence substantially dependent upon molecular weight.

In one aspect, the apparatus comprises a portable unit which can be transported to, and used to measure fluorescence from, a polymer which is part of a larger, and relatively fixed, structure.

In an embodiment, the light irradiating the sample comprises at least one substantially monochromatic wavelength in the range of about 200 to 500 NM. More preferably, the light irradiating the sample comprises at least one substantially monochromatic wavelength in the range of about 270 to 350 NM. More preferably, the light irradiating the sample comprises at least one substantially monochromatic wavelength in the range of about 290 to 330 NM. More preferably, the light irradiating the sample comprises at least one substantially monochromatic wavelength in the range of about 300 to 320 NM. More preferably, the light irradiating the sample comprises a wavelength of about 310 NM.

In an embodiment, radiation monitored by the detector comprises a wavelength range of about 200 to 900 NM. More preferably, radiation monitored by the detector comprises a wavelength range of about 310 to 600 NM. In an embodiment, radiation monitored by the detector comprises wavelengths of about 380 and 500 NM.

Preferably, the polymer comprises aromatic hydroxyl groups. More preferably, the polymer comprises melt polycarbonate. In yet another embodiment, the apparatus comprises a filter.

In yet another aspect, the invention comprises computer readable media comprising software code for controlling the apparatus of the invention.

Thus, the invention comprises using fluorescence to rapidly and non-invasively determine the hydrolytic stability and degradation of molecular weight in polycarbonate samples. Early studies attempting to use luminescence to measure polymer molecular weight have been limited (see Allen, N. S., in *Analysis of Polymer Systems*, Chapter 4, Eds. L. S. Bark and N. S. Allen, Applied Science Publishers Ltd., London (1982)). For example, polymer degradation has been evaluated by monitoring the fluorescence associated with known polymer degradation products such as phenyl-o-phenoxybenzoate and dihydroxybenzophenone (Chipalkatti, M. K. and J. J. Laski, in *Structure-Property Relations in Polymers, Spectroscopy and Performance*, Chapter 25, pp 623–642, Eds: M. W. Urban and C. D. Craver, American Chemical Society, Washington, D.C. (1993)). Also, it has been shown that under certain conditions, polystyrene fluorescence may be inversely correlated with molecular weight (Gachkovskii, V. F., *Polym. Sci.* (USSR) 2199 (1965); original source, *Vysokomol. Soedin.*, 7(12):2009, (1965); discussed in Allen, N. S. (1982)). None of these studies, however, show a direct correlation between fluorescence and polycarbonate molecular weight. In addition, none of these studies provide the capability to determine polymer molecular weight in the presence of additives commonly used in polymers to achieve desired engineering properties, such as flame retardation, UV stability, and others.

In other studies, fluorescence spectroscopy has been used to identify and characterize commercial polymers, (see e.g. Allen N. S. and J. F. McKellar, *Chemistry and Industry*, 2:907–913 (1978); Allen, N. S., et al., *Analyst* 101:260–264 (1976); and Allen, N. S. (1982)); for flash photochemical studies of polycarbonate and related model compounds (Humphrey, J. S., et al., *Macromolecules* 6: 305–314 (1973)), identification of initial salicylate photo-Fries rearrangement products of polycarbonate (Hoyle, C. E., et al., *J. Polym. Sci. A: Polym. Chem.* 30:1525–33 (1992)), detection of salicylic and 2,2'-bisphenol type products in the very early stage of polycarbonate photolysis (Shah, H., et al., *Macromolecules,* 27:553–561 (1994)), investigation of solvent effects on the photophysics of bisphenol-A-based polycarbonate and diphenylcarbonate (Hoyle, C. E., et al., *Can. J. Chem.,* 73:2062–68 (1995)), studies of the photochemistry and photodegradation of polycarbonate (Pankasem, S., et al., *Macromolecules* 27:3773–81 (1994)), and identification of fluorescent products produced by thermal treatment of bisphenol-A-based polycarbonate (Rufus, I. B., et al., *J. Appl. Polym. Sci.* 51:1549–58 (1994)).

Figure 1:
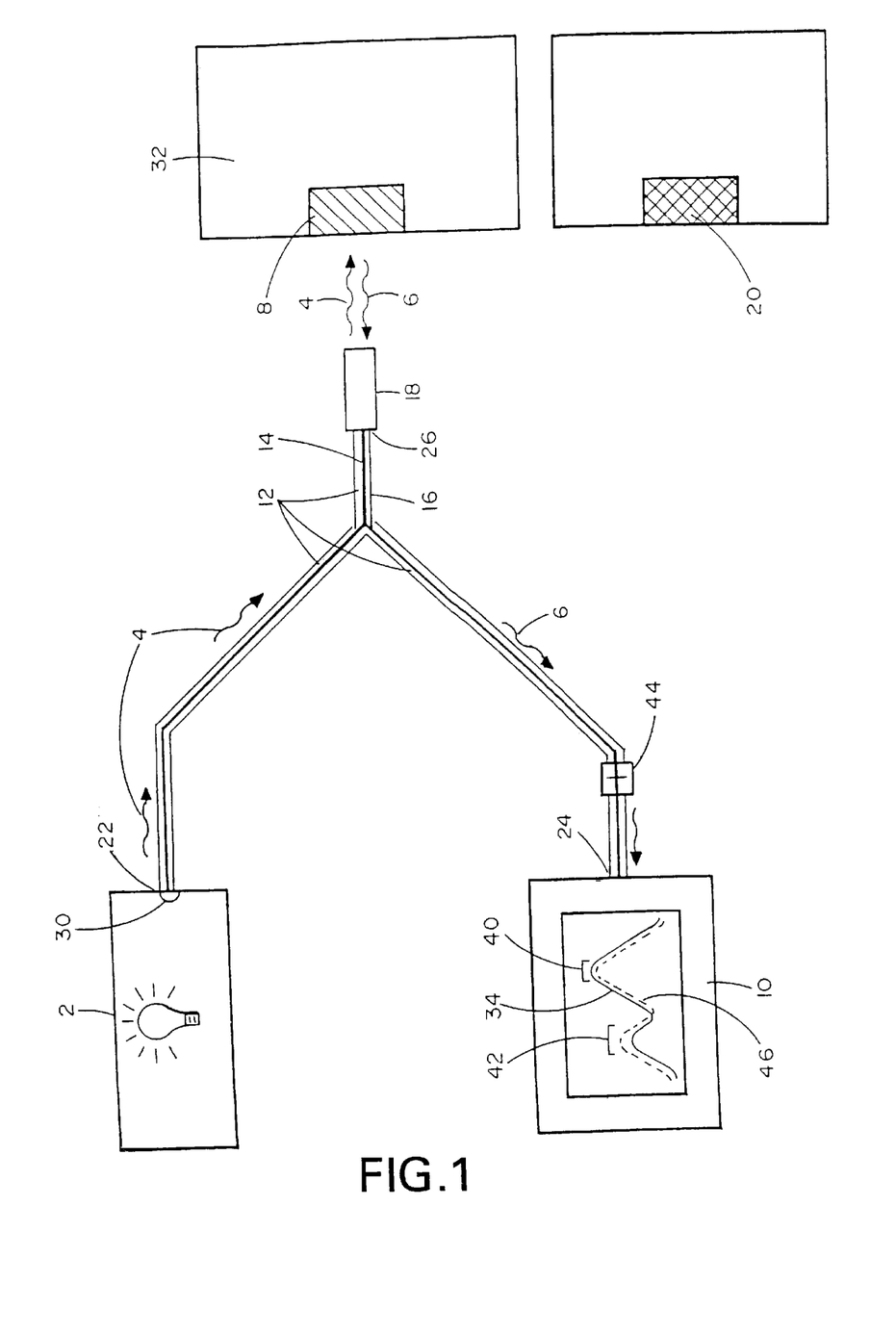
FIG. 1 is a representation of an embodiment of the method and apparatus of the invention.

Referring now to FIG. 1, in an embodiment, the apparatus of the invention comprises a light source 2, wherein substantially monochromatic light 4 emitted by light source 2 irradiates a polymer sample 8. Typical light sources which include UV, visible, and near IR ranges are shown in Table 1. As recognized by those of ordinary skill in the art, and discussed in more detail herein, sources comprising selected ranges of irradiating wavelengths are used for excitation of polymer fluorescence. In an embodiment, light source 2 may include a focusing element 30 to focus the excitation radiation. Focusing element 30 is preferably a lens made of quartz or other UV-transparent material.

TABLE 1

Light sources useful for excitation of fluorescence

| Source | Spectral range of emission (NM) |
|---|---|
| Continuous wave sources: | |
| Xenon arc lamp | 200–1000 |
| Mercury arc lamp | 250–600 |
| Deuterium lamp | 180–420 |
| Tungsten lamp | 320–2500 |
| Light emitting diodes | different diodes cover range from 370 to 1500 NM |
| Diode lasers | different diode lasers cover range from about 400 to 1500 NM |
| Argon ion laser | several lines over 350–514 NM |
| Helium-neon laser | several lines over 543–633 NM |
| Krypton laser | several lines over 530–676 NM |
| Pulsed sources: | |
| Nitrogen laser | 337 NM |
| Nd:YAG laser | fundamental - 1064, frequency doubled- 532, tripled - 355 |
| Ti: Sapphire laser | 720–1000, frequency doubled 360–500 |
| Dye lasers | 360–990 frequency doubled 235 to 345 |

Figure 2:
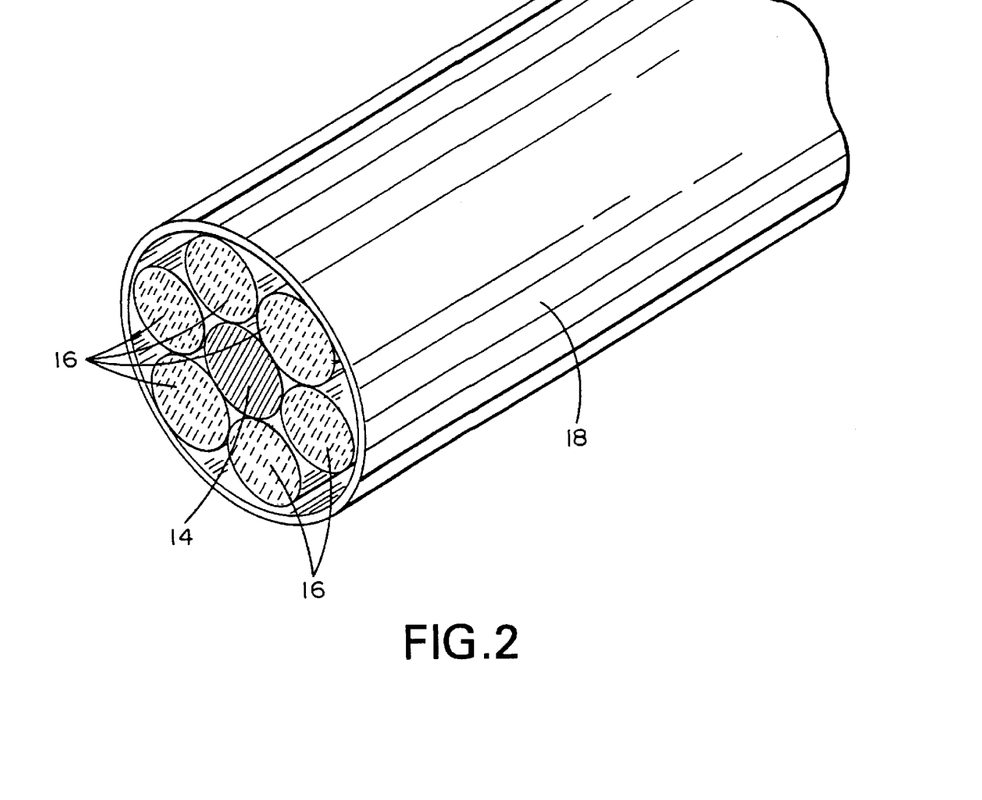
FIG. 2 is a representation of an aspect of an embodiment of the apparatus of the invention.

A detector 10 monitors fluorescent radiation 6 emitted by the irradiated polymer. The apparatus further comprises a probe 18 for illuminating the polymer sample. In an embodiment, probe 18 comprises a fiber optic bundle 12 having at least one illuminating fiber 16 and at least one collecting fiber 14. Thus, probe 18 may comprise multiple illuminating fibers 16, multiple collecting fibers 14, or multiple illuminating fibers 18 and multiple collecting fibers 14. For example, in an embodiment, and referring now to FIG. 2, probe 18 comprises six illuminating fibers 16 circumferentially placed around one collecting fiber 14. More preferably, and referring again to FIG. 1, fiber optic bundle 12 is bifurcated such that it is connected at one end 22 to light source 2 and at the other end 24 to detector 10. Preferably, detector 10 is a spectrofluorometer or other imaging tool capable of quantitating radiation. Probe 18 for illuminating the polymer sample preferably comprises the single end 26 of said bifurcated fiber optic bundle 12.

In an embodiment, light 4 travels from light source 2 by illuminating fibers 16 of fiber optic bundle 12 and exits at probe 18 to irradiate sample 8. Upon excitation of sample 8 with incident radiation 4, the sample emits fluorescent radiation 6. Emitted radiation 6 is preferably dependent on the composition of polymer sample 8. Emitted radiation 6 is then collected by probe 18 and transmitted by at least one collecting fiber 14 to detector 10. In an embodiment, detector 10 quantitates emitted radiation 6. In an embodiment, emitted radiation 6 is correlated to polymer molecular weight. More preferably, emitted radiation 6 is diagnostic of polymer hydrolysis.

In summary, in a preferred embodiment, light 4 from light source 2 is transmitted by illuminating fibers 16 to probe 18. Probe 18 emits light 4 which irradiates polymer sample 8, and fluorescent light 6 emitted by sample 8 is collected by probe 18 and transmitted by collecting fiber 14 to detector 10. In an embodiment, light source 2 is a 450-W Xe arc lamp coupled to a monochromator for wavelength selection of the excitation light.

Figure 3:
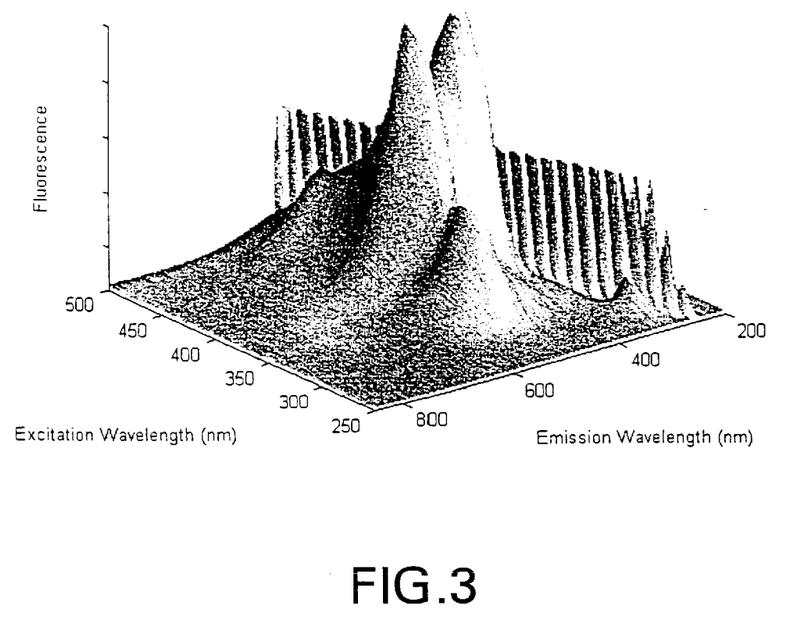
FIG. 3 is a representation of an embodiment of the method and apparatus of the invention which illustrates a fluorescence excitation-emission map of a solid melt polycarbonate.

Referring now to FIG. 3, the spectral emission 34 is dependent upon the excitation wavelength 4 employed. Generally, election of spectral ranges for the excitation of polycarbonate and for collection of fluorescence emission is complicated by the presence of multiple fluorescing species in the sample. For example, for melt polycarbonate, fluorescing species include monocapped bisphenol A (BPA), small hydroxyl terminated oligomers, cyclics and others. Thus, samples are irradiated with light of at least one monochromatic wavelength and emission spectra measured either for a single excitation wavelength or for several excitation wavelengths in sequence. For example, and referring again to FIG. 3, emission spectra may comprise one or several planes from the three dimensional excitation/emission map. Preferably, for measurement of polymer molecular weight, irradiating light 4 comprises at least one substantially monochromatic wavelength of about 200 to 550 NM. More preferably, irradiating light 4 comprises at least one substantially monochromatic wavelength of about 270 to 350 NM. More preferably, irradiating light 4 comprises at least one substantially monochromatic wavelength of about 290 to 330 NM. More preferably, irradiating light 4 comprises at least one substantially monochromatic wavelength of about 300 to 320 NM. More preferably, irradiating light 4 comprises a wavelength of about 310 NM.

In one aspect, the apparatus is used for in situ monitoring of polymer samples which are constituents of a larger structure. For example, and referring back to FIG. 1, probe 18 may be used to irradiate and collect fluorescence 6 from a polycarbonate sample 8 which is part of a larger structure 32. Preferably, the analysis is performed without removing polymer 8 from larger structure 32. For this type of in situ analysis, a certain portion of the excitation light 4 from fiber-optic probe 18 may be reflected back from the structure being analyzed, thereby competing with the sample fluorescence 6 measured. If the wavelength of the excitation light 4 is close to the wavelength of the emitted fluorescence 6, the excitation light 4 may contribute to elevated background in selected regions of the fluorescence spectrum 34, thereby reducing the precision of measurements. To overcome the problems of sample reflectance of excitation light, in an embodiment, fiber-optic probe 18 is tilted. In another embodiment, a long-pass (LP) emission filter 44 is included to block the reflected excitation light.

In another aspect, the invention comprises a method for the rapid, nondestructive determination of hydrolytic stability of polymers comprising irradiating a polymer sample with light of a substantially monochromatic excitation wavelength, wherein the excitation wavelength used for irradiation is selected based upon an analysis of multiple emission spectra of the polymer irradiated at multiple excitation wavelengths; collecting fluorescent radiation emitted by the irradiated polymer sample at each excitation wavelength; monitoring emitted radiation which is substantially dependent upon polymer molecular weight; comparing radiation emitted by the irradiated polymer sample with radiation emitted from a similarly irradiated control polymer known to be substantially free of hydrolytic cleavage; and correlating a decrease of the emitted radiation substantially dependent upon polymer molecular weight to hydrolysis of the polymer sample.

Thus, referring again to FIG. 1, in an embodiment, the invention comprises irradiation of a polymer sample 8 with light of a defined excitation wavelength 4. Light emitted 6 from the irradiated polymer 8 is then collected, by for example probe 18, and transmitted to a detector 10. Preferably, light emitted 6 from the polymer sample 8 is fluorescent light. More preferably, detector 10 generates a signal 34 characteristic of polymer 8. Thus, in an embodiment, signal 34 comprises at least one discrete wavelength or band of wavelengths. In an embodiment, signal 34 comprises a spectrum. Preferably, signal 34 comprises a spectral maximum 42 which is substantially dependent upon polymer molecular weight. Preferably, spectral maximum 42 substantially dependent upon polymer molecular weight is distinguished from other regions of signal 34.

In an embodiment, and still referring to FIG. 1, the spectra from polymer sample 8 is compared to the spectra from a control polymer 20 known to be without substantial hydrolytic degradation. Preferably, control polymer 20 comprises a polymer substantially similar to polymer sample 8, but which has not been exposed to hydrolytic conditions. More preferably, control polymer 20 generates a spectral emission 46 distinct from spectral emission 34 for polymer sample 8.

For the measurement to be applicable, aromatic hydroxyl (OH) groups should be present in the polymer. Thus, in a preferred embodiment of the invention, polymer sample 8 comprises polycarbonate, polyester, and other aromatic polymers and their blends and copolymers.

Measurement of sample fluorescence generally provides for a much broader range of sample size and geometry than are possible for transmission measurements. In addition, fluorescence measurements provide detection limits which are on the order of 100–1000 times more sensitive than transmission measurements (see e.g. Ingle, J. D. and S. R. Crouch (1988)). Thus, only a fraction of the sample required for transmission measurements is required for determination of hydrolytic stability by fluorescence. Importantly, in contrast to transmission measurements, sample geometry and local variations in sample density or thickness do not affect fluorescence. Also, colored samples are easily evaluated by fluorescence, because absorption wavelengths for color are significantly longer than, and thus do not interfere with, the spectral range used in the invention. Thus, the use of fluorescence to determine hydrolytic stability is preferably applicable to a polycarbonates of weight average molecular weight (MW) ranging from about 15,000 to 50,000.

In an embodiment, fluorescence detection is capable of precise measurements in the presence of impurities by using a variety of known fluorescence signal generation methods including, but not limited to, excitation-emission mapping, synchronous detection, and derivative detection. These methods preferably are used to distinguish fluorescence changes due to physical weathering of the sample from those due to hydrolysis (see e.g. Ingle, J. D. and S. R. Crouch (1988)).

Figure 4:
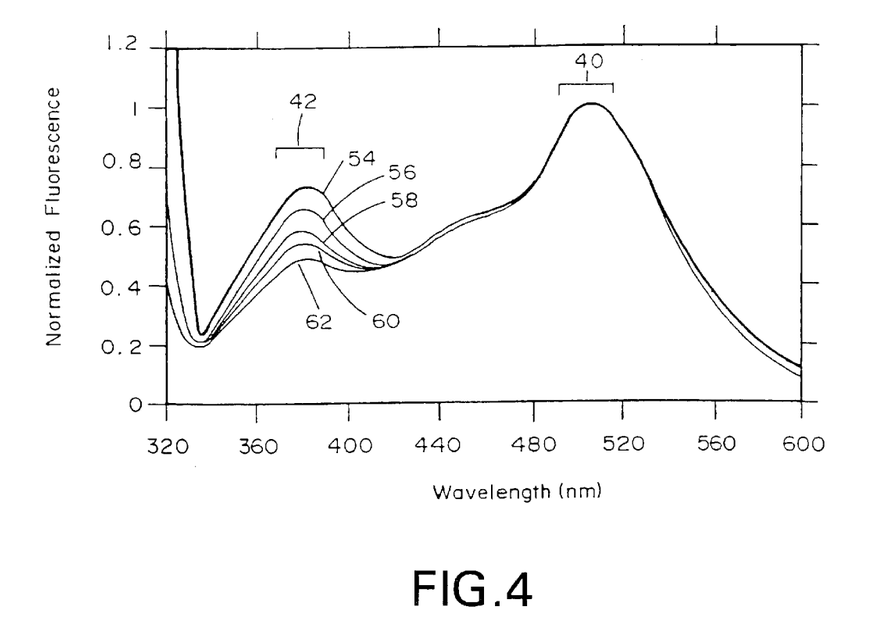
FIG. 4 illustrates an embodiment of the method of the invention in which the fluorescence spectra of polycarbonate samples exposed to increasing time periods of hygrothermal conditions (autoclaving) are compared.

Referring now to FIG. 4, in an embodiment, a spectrum is generated for each sample. Preferably, polymers comprising different levels of hydrolysis comprise differently shaped spectra. Thus, polymers having no exposure to hydrolytic conditions 54 have a differently shaped spectra than samples of the same polymer formulation 56, 58, 60 and 62, respectively, which have increasing exposure to hydrolytic conditions. Preferably, the spectral change corresponds to a change in selected region of the spectrum 42 corresponding to polymer molecular weight. More preferably, an increase in polymer hydrolysis is associated with a decrease in the spectral maxima 42 corresponding to polymer molecular weight. Thus, samples that have no exposure to hydrolytic conditions 54 comprise a greater fluorescence intensity at spectral region 42 corresponding to polymer molecular weight than samples 56, 58, 60 and 62, respectively, which have increasing exposure to hydrolytic conditions.

Because selection of spectral ranges for the excitation of polycarbonate and for collection of fluorescence emission can be complicated by the presence of multiple fluorescing species in the sample, the spectral emission corresponding to polymer molecular weight is preferably dependent upon the excitation wavelength employed (see FIG. 3). In a an embodiment, light 4 irradiating polymer 8 comprises at least one excitation wavelength in the range of about 200 to 550 NM. More preferably, light 4 irradiating polymer 8 comprises at least one excitation wavelength in the range of about 270 to 350 NM. More preferably, light 4 irradiating polymer 8 comprises at least one excitation wavelength in the range of about 290 to 330 NM. More preferably, light 4 irradiating polymer 8 comprises at least one excitation wavelength in the range of about 300 to 320 NM. Even more preferably, light 4 irradiating polymer 8 comprises an excitation wavelength of about 310 NM.

In an embodiment, the monitored radiation comprises a wavelength of 200 to 900 NM. Preferably, the monitored radiation comprises a wavelength of about 310 to 600 NM. More preferably, the spectral region substantially dependent upon polymer molecular weight comprises a wavelength of about 360 to 420 NM. Even more preferably, the spectral region substantially dependent upon polymer molecular weight comprises a wavelength of about 380 NM.

Referring again to FIG. 4, in one aspect, the method comprises determining the ratio of the intensity of emitted fluorescence due to polymer molecular weight to the intensity of emitted fluorescence due to a component of the polymer which not affected by hydrolysis and thereby constitutes an internal standard. Preferably, the fluorescence signal due to the internal standard can be separated from the fluorescence signal due to molecular weight. For example, Fries rearrangement products are often present in polycarbonates synthesized in melt polymerization reactions. Fries rearrangement products result from conversion of phenolic esters into corresponding ortho and para hydroxyketones as a result of the inherent stability of polybenzenoid compounds. In an embodiment, Fries products have a fluorescence maxima at about 500 NM. Because Fries products are not reduced by polymer hydrolysis, the fluorescence of Fries products at about 500 NM can be utilized as an internal standard. Fries products may also be used as an internal reference in other polycarbonates such as interfacial polycarbonates (LF), although the amount of Fries may be less than that found in melt polycarbonate. Similarly, other polymers may comprise alternative internal standards.

Thus, in an embodiment, spectra are normalized by scaling individual spectra with respect to a common band. For example, and referring again to FIG. 4, in an embodiment, fluorescence band 40 at about 500 NM is correlated with Fries products and fluorescence band 42 at about 380 NM is correlated with polymer molecular weight. To enable a direct comparison of discrete spectra, band 50 at 500 NM is assigned a relative value of 1.0 and other spectral values are scaled accordingly.

Figure 5:
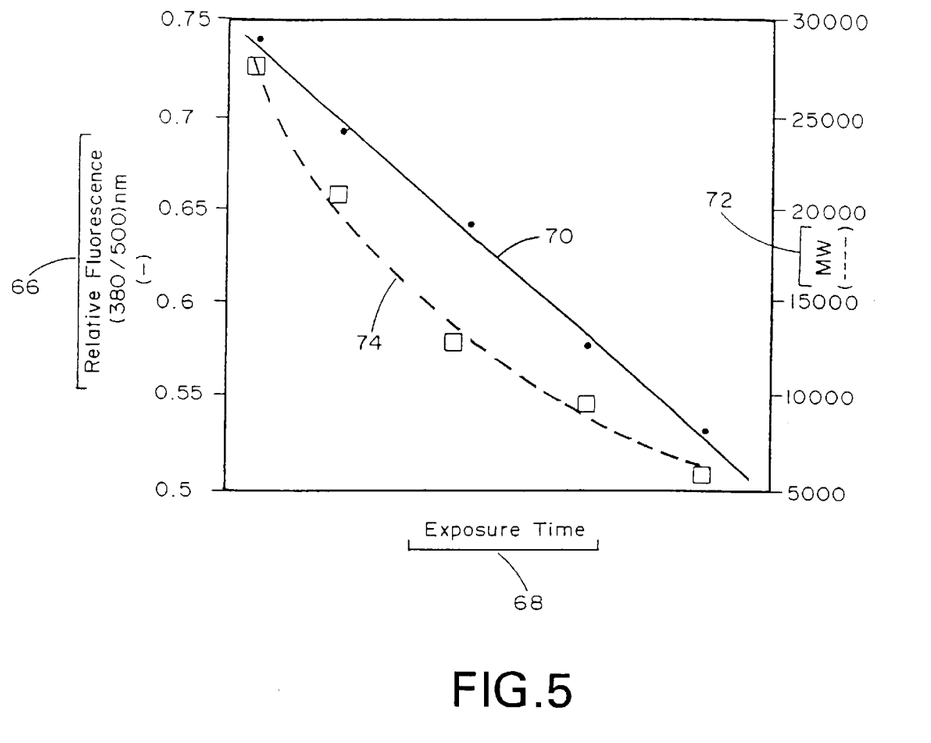
FIG. 5 is a representation of an embodiment of the method of the invention in which the relative fluorescence at 380 NM to 500 NM (•), and the molecular weight of polycarbonate samples ( ) are compared to the time of exposure to hygrothermal conditions (autoclaving)

Thus, in an embodiment, and referring now to FIG. 5, reduction of fluorescence due to loss of polymer molecular weight is expressed as the ratio of fluorescence intensity at about 380 NM to 500 NM ($I_{380}/I_{500}$) 66 and plotted as a function of exposure to hygrothermal conditions 68. Hygrothermal conditions may include, but are not limited to, autoclaving at 120° C. for 24 hours at a pressure of 1 bar and 100% relative humidity. This method of analysis inherently incorporates normalization of spectra by the fluorescence intensity at 500 NM. Preferably, the $I_{380}/I_{500}$ fluorescence intensity ratio 66 will be correlated 70 with exposure of the polymer to hygrothermal conditions 68. More preferably, the $I_{380}/I_{500}$ ratio 66 will be correlated 74 to polymer hydrolysis and loss of molecular weight 72. Thus, in an embodiment, increasing exposure of a polymer to hygrothermal conditions 68 is associated with a decrease in the $I_{380}/I_{500}$ ratio 70 and a corresponding decrease 74 in polymer molecular weight. Preferably, the decrease in the $I_{380}/I_{500}$ fluorescence intensity ratio 70 with exposure to hygrothermal conditions is substantially linear.

Figure 6:
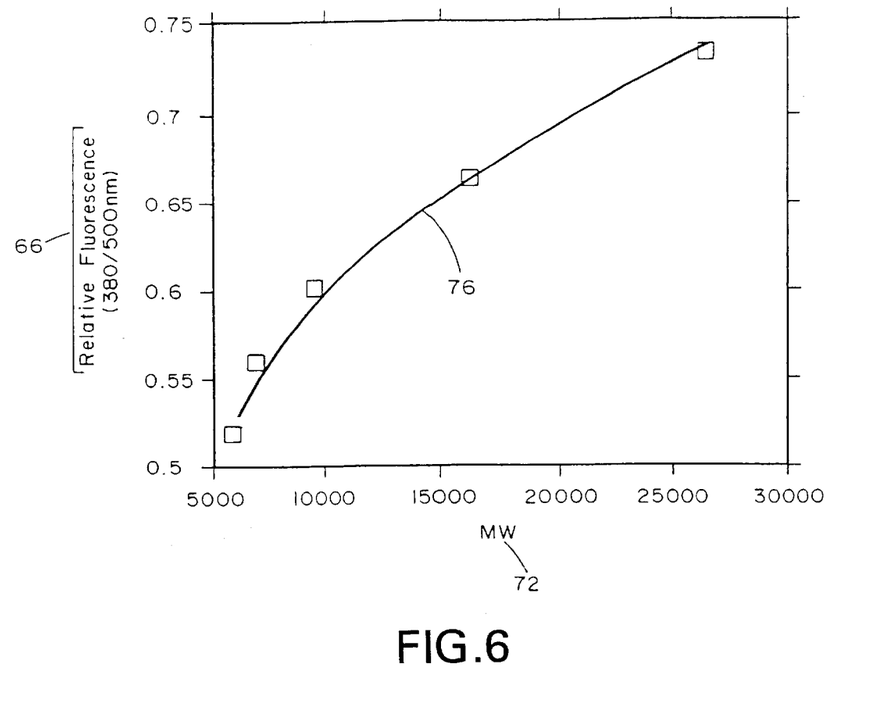
FIG. 6. illustrates an aspect of an embodiment of the method of the invention comprising the correlation between relative fluorescence at 380 NM to 500 NM ($I_{380}/I_{500}$ ratio) and polymer molecular weight (MW) for a sample treated for increasing time periods of hygrothermal conditions.

In an embodiment, and referring now to FIG. 6, changes in the $I_{380}/I_{500}$ fluorescence intensity ratio 66 are directly correlated 76 to changes in polymer molecular weight 72. Preferably, the $I_{380}/I_{500}$ relative fluorescence intensity ratios 66 are measured for a polymer having various levels of hygrothermal exposure, and used to generate a univariate model 76 relating the $I_{380}/I_{500}$ fluorescence intensity ratio 66 to polymer molecular weight 72. This type of model can be developed for any polymer of interest. Preferably, a database of models, each relating the $I_{380}/I_{500}$ fluorescence intensity ratio 66 to polymer molecular weight 72 are developed. Once the relationship between $I_{380}/I_{500}$ fluorescence intensity ratio and polymer molecular weight has been determined, the $I_{380}/I_{500}$ fluorescence intensity ratio for a polymer exposed to weathering or hydrolytic conditions can be used to predict the reduction in molecular weight (hydrolytic degradation) for that sample. This information may then be used to calculate the useful lifetime remaining for the polymer sample. For example, and referring to FIG. 6, univariate or multivariate models may be generated for a selected group of polymers for which field testing is appropriate. It can be seen that the model used to predict sample molecular weight based upon an observed $I_{380}/I_{500}$ ratio can also be used to predict the $I_{380}/I_{500}$ ratio for a polymer sample of given molecular weight. Thus, for the model shown in FIG. 6, a polymer of less than 15,000 molecular weight would be expected to have a $I_{380}/I_{500}$ ratio of less than 0.65. The measured $I_{380}/I_{500}$ value is then applied to the model correlating the $I_{380}/I_{500}$ ratio to exposure time (FIG. 4) to predict the exposure time required for the polymer to degrade to a molecular weight of 15,000 or less under the same hygrothermal conditions.

Thus, using the apparatus and method of the invention, a nondestructive quantitative measurement of polymer hydrolysis is possible. Using an embodiment of the method and apparatus of the invention, a polymer sample is irradiated and the $I_{380}/I_{500}$ fluorescence intensity ratio determined. The $I_{380}/I_{500}$ fluorescence intensity ratio for a polymer sample is compared to the $I_{380}/I_{500}$ fluorescence intensity ratio for a control. Preferably, the control is substantially similar to the polymer sample but has not been exposed to hydrolytic conditions. More preferably, the molecular weight of the control is known. Even more preferably, the $I_{380}/I_{500}$ fluorescence intensity ratio is directly correlated to polymer molecular weight, so that the measurements provide qualitative information about polymer hydrolytic stability. By measuring the $I_{380}/I_{500}$ fluorescence intensity ratio and evaluating the data using the model developed for that polymer, a quantitative estimate of polymer molecular weight and hydrolytic degradation is possible. The data is then used to calculate the useful lifetime of the polymer based on the extent of hydrolysis and molecular weight degradation. Univariate or multivariate models may also be developed for rapid analysis of combinatorial polymer libraries. In an embodiment, the general correlation between the fluorescence intensity ratio and loss of polymer molecular weight is valid over a range polymer molecular weight. Preferably, by measuring fluorescence at only two discrete wavelengths, automation is simplified.

As will be recognized by those of ordinary skill in the art, all or part of the steps in the method of the present invention may be coded or otherwise written in computer software, in a variety of computer languages including, but not limited to, C, C++, Pascal, FORTRAN, Visual Basic, Microsoft Excel, MATLAB, Maple, Mathematica, and Java. Accordingly, additional aspects of the present invention include computer software for performing one or more of the method steps set forth herein. The software code may be compiled and stored in executable form on computer readable media as, for example, computer ROM, floppy disk, optical disk, hard disks, CD ROM, or the like.

For example, an embodiment of a system for performing the methods of the invention comprises a portable unit which includes a light source connected to a monochromator and a probe for irradiation of a polycarbonate panel included as part of a larger structure. By monitoring fluorescence emitted by the panel, determining the $I_{380}/I_{500}$ fluorescence intensity ratio, and comparing the measured value to the model developed for that polymer, the operator is provided with a quantitative estimate of hydrolytic degradation and an estimate of the remaining useful lifetime of the polymer. The entire system, or any part of the system, can be controlled by a computer and software specifically designed to implement a particular embodiment of the method. Thus, any and all steps of the method, including, but not limited to, irradiation of samples, collection of fluorescent spectral data, collating and processing of the data, and final statistical analysis, may be specifically programmed and controlled by a computer.

Features and advantages of the inventive concept covered by the present invention are illustrated in the following methods and example.

EXAMPLE

The following example illustrates an embodiment of the invention in which reduction in polymer molecular weight as a function of exposure to hygrothermal conditions is correlated to a decrease in the ratio of fluorescence at 380 NM to 500 NM (the $I_{380}/I_{500}$ fluorescence intensity ratio). Measurements were performed on a setup which included a white light source (450-W Xe arc lamp, Model FP-024; SLM Instruments, Inc., Urbana, Ill.), a monochromator for selection of the excitation wavelength (Model FP-092; SLM Instruments, Inc., Urbana, Ill.), and a portable spectrofluorometer (Model ST2000; Ocean Optics, Inc., Dunedin, Fla.).

The spectrofluorometer was equipped with a 200-μm slit, 600-grooves/mm grating blazed at 400 NM and covering the spectral range from 250 to 800 NM with efficiency greater than 30%, and a linear CCD-array detector. Excitation light from the monochromator was focused into one of the arms of a "six-around-one" bifurcated fiber-optic reflection probe (Model R400-7-UV/VIS; Ocean Optics, Inc., Dunedin, Fla.). Emission light was collected from a sample when the common end of the fiber-optic probe was positioned near the sample at a certain angle to minimize the amount of excitation light reflected from the sample back into the probe. The second arm of the probe was coupled to the spectrofluorometer. Collected spectra were not corrected for instrument spectral response such as light source spectrum, spectral sensitivity of the CCD, and spectra transmission of the fiber optic bundle.

Samples were autoclaved at 1 bar pressure, 120° C., and 100% humidity for increasing amounts of time as indicated in the tables below. Number average molecular weight (Mn) and weight average molecular weight (MW) were obtained by gel permeation chromatography (GPC) against polystyrene standards. Column temperature was 25□ C. and the mobile phase was chloroform.

It can be seen (Table 2) that increasing exposure of the polycarbonate sample to hygrothermal conditions resulted in polymer hydrolysis as measured by a decrease in both weight and number average molecular weight.

TABLE 2

| Sample # | Exposure (h) | Mn | MW |
|---|---|---|---|
| 5 | 0 | 10289 | 26177 |
| 4 | 24 | 6264 | 15868 |
| 3 | 48 | 4013 | 9960 |
| 2 | 72 | 2951 | 7188 |
| 1 | 96 | 2381 | 5747 |

Increasing exposure to hydrothermal conditions was also associated with a reduction of fluorescent intensity at 380 NM as compared to 500 NM. Results are shown in FIGS. 4 and 5, and are tabulated as the ratio of fluorescent intensity at 380 NM to 500 NM ($I_{380}/I_{500}$) in Table 3 below. A plot showing the correlation between the $I_{380}/I_{500}$ fluorescence intensity ratio and polymer molecular weight is shown as FIG. 6. By taking a ratio of two distinct signals, spectra are inherently normalized with respect to variations due to instrument variability and other external variables such as sample size, shape and the like.

TABLE 3

| Sample # | Exposure (h) | $I_{380}/I_{500}$ 1 | $I_{380}/I_{500}$ 2 | $I_{380}/I_{500}$ 3 | Mean | Standard Deviation |
|---|---|---|---|---|---|---|
| 5 | 0 | 0.731 | 0.731 | 0.732 | 0.731 | 0.000882 |
| 4 | 24 | 0.667 | 0.667 | 0.663 | 0.666 | 0.00247 |
| 3 | 48 | 0.610 | 0.609 | 0.608 | 0.609 | 0.00118 |
| 2 | 72 | 0.569 | 0.566 | 0.563 | 0.566 | 0.00314 |
| 1 | 96 | 0.519 | 0.516 | 0.513 | 0.516 | 0.00334 |

It will be recognized by those of ordinary skill in the art that advantages of the fluorescence method disclosed here over other methods for the screening of degradation of polymer molecular weight include:

1. Qualitative and quantitative assessment of the hydrolytic stability of polymer preparations;

2. An apparatus and method to assess hydrolytic degradation of polymer samples in situ;

3. Short analysis time;

4. Nondestructive methods allowing measurements to be performed on solid polymer without destruction of sample and without generation of environmentally hazardous waste;

5. High-throughput analysis capable of automation;

6. Sample size which is 100 to 1,000 times less than that required for other types of analyses; and 7. No restraints on sample geometry or thinness.

It will be understood that each of the elements described above, or two or more together, may also find utility in applications differing from the types described herein. While the invention has been illustrated and described as embodied in an apparatus and method for rapid, high-throughput, nondestructive analysis of polymer hydrolysis, it is not intended to be limited to the details shown, since various modifications and substitutions can be made without departing in any way from the spirit of the present invention. For example, robotics equipment can be used to prepare the samples and various types of parallel analytical screening methods can be incorporated. Also, it is contemplated that other parameters besides Fries products can be used as an internal standard. Similarly, it is contemplated that other parameters besides polymer molecular weight can be assessed using the techniques described herein. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method for the nondestructive determination of hydrolytic stability of polymers, wherein the polymers, when hydrolyzed, create aromatic hydroxyl groups, comprising:

irradiating a polymer sample with light of at least one substantially monochromatic excitation wavelength, wherein the excitation wavelengths used for irradiation are selected based upon an analysis of multiple emission spectra of the polymer irradiated at multiple excitation wavelengths;

collecting fluorescent radiation emitted by the irradiated polymer sample for each excitation wavelength;

monitoring emitted radiation which is substantially dependent upon polymer molecular weight;

comparing monitored radiation emitted by the irradiated polymer sample with monitored radiation emitted from a similarly irradiated control polymer known to be substantially free of hydrolytic cleavage; and correlating a change of the emitted radiation substantially dependent upon polymer molecular weight to hydrolysis of the polymer sample.

2. The method of claim 1, further comprising applying a predetermined selection test to determine whether the sample exhibits a desired resistance to hydrolysis-induced degradation.

3. The method of claim 1, further comprising the step of calculating a useful lifetime of the sample.

4. The method of claim 1, wherein the irradiating light comprises at least one substantially monochromatic wavelength in the range of about 200 to 550 nm.

5. The method of claim 1 wherein the irradiating light comprises at least one substantially monochromatic wavelength in the range of about 270–350 nm.

6. The method of claim 1, wherein the irradiating light comprises at least one substantially monochromatic wavelength in the range of about 290 to 330 nm.

7. The method of claim 1, wherein the irradiating light comprises at least one substantially monochromatic wavelength in the range of about 300 to 320 nm.

8. The method of claim 1, wherein the irradiating light comprises a wavelength of about 310 nm.

9. The method of claim 1, wherein the monitored radiation comprises a wavelength of about 200 to 900 nm.

10. The method of claim 1, wherein the monitored radiation comprises a wavelength of about 310 to 600 nm.

11. The method of claim 1, wherein the emitted radiation substantially dependent upon polymer molecular weight comprises a wavelength in the range of about 360–420 nm.

12. The method of claim 1, wherein the emitted radiation substantially dependent upon polymer molecular weight comprises of a wavelength of about 380 nm.

13. The method of claim 1, wherein the emitted radiation substantially dependent upon molecular weight is scaled relative to emitted radiation which is substantially independent of sample hydrolysis.

14. The method of claim 13, wherein the emitted radiation which is substantially independent of sample hydrolysis comprises fluorescence due to Fries product.

15. The method of claim 13, wherein the emitted radiation substantially independent of polymer hydrolysis comprises of a wavelength of about 500 nm.

16. The method of claim 1, wherein the polymer comprises melt polycarbonate.

17. Computer readable media comprising software code for performing the method of claim 1.

18. A method for nondestructive determination of hydrolytic stability of polymers, wherein the polymers, when hydrolyzed, create aromatic hydroxyl groups, comprising:
    irradiating a polymer sample with light of at least one substantially monochromatic excitation wavelength, wherein the excitation wavelengths used for irradiation are selected based upon an analysis of multiple emission spectra of the polymer irradiated at multiple excitation wavelengths;
    monitoring fluorescent light emitted by the irradiated polymer sample at each excitation wavelength;
    defining at least one wavelength comprising emitted fluorescence which is substantially dependent upon polymer molecular weight;
    defining at least one wavelength comprising emitted fluorescence which is substantially independent of polymer molecular weight;
    scaling fluorescence which is substantially dependent upon polymer molecular weight relative to fluorescence which is substantially independent of sample molecular weight; and
    correlating the scaled fluorescence to sample hydrolysis.

19. The method of claim 18, further comprising applying a predetermined selection test to the scaled fluorescence to determine whether the sample exhibits a desired resistance to hydrolysis-induced degradation.

20. The method of claim 18, further comprising calculating a useful lifetime for the polymer sample.

21. The method of claim 18, wherein the polymer comprises melt polycarbonate.

22. The method of claim 18, wherein the fluorescence substantially independent of polymer molecular weight comprises fluorescence due to Fries products.

23. The method of claim 18, wherein the irradiating light comprises at least one substantially monochromatic wavelength in the range of about 250 to 500 nm.

24. The method of claim 18, wherein the irradiating light comprises at least one substantially monochromatic wavelength in the range of about 270 to 350 nm.

25. The method of claim 18, wherein the irradiating light comprises at least one substantially monochromatic wavelength in the range of about 290 to 330 nm.

26. The method of claim 18, wherein the irradiating light comprises at least one substantially monochromatic wavelength in the range of about 300 to 320 nm.

27. The method of claim 18, wherein the irradiating light comprises a wavelength of about 310 nm.

28. The method of claim 18, wherein the monitored radiation comprises a wavelength in the range of about 200 to 900 nm.

29. The method of claim 18, wherein the monitored radiation comprises a wavelength in the range of about 310 to 600 nm.

30. The method of claim 18, wherein the fluorescence substantially dependent upon polymer molecular weight comprises a wavelength of about 360 to 420 nm.

31. The method of claim 18, wherein the fluorescence substantially dependent upon polymer molecular weight comprises a wavelength of about 380 nm.

32. The method of claim 18, wherein the fluorescence substantially independent of polymer molecular weight comprises a wavelength of about 500 nm.

33. Computer readable media comprising software code for performing the method of claim 18.

34. An apparatus for the nondestructive monitoring of hydrolytic stability of polymers, wherein the polymers, when hydrolyzed, create aromatic hydroxyl groups, comprising:
    a light source, wherein said light source irradiates a polymer sample with at least one wavelength of substantially monochromatic light;
    a probe, wherein said probe transmits light from said light source to irradiate said polymer sample, and collects fluorescent radiation emitted by said polymer sample; and
    a detector, wherein said detector monitors radiation emitted by said sample comprising fluorescence substantially dependent upon polymer molecular weight.

35. The apparatus of claim 34, wherein said apparatus further comprises a portable unit which can be transported to, and used to measure fluorescence from, a polymer which is part of a larger structure.

36. The apparatus of claim 34, wherein said light irradiating said polymer sample comprises at least one substantially monochromatic wavelength in the range of about 200 to 550 nm.

37. The apparatus of claim 34, wherein said light irradiating said polymer sample comprises at least one substantially monochromatic wavelength in the range of about 270 to 350 nm.

38. The apparatus of claim 34, wherein said light irradiating said polymer sample comprises at least one substantially monochromatic wavelength in the range of about 290 to 330 nm.

39. The apparatus of claim 34, wherein said light irradiating said polymer sample comprises at least one substantially monochromatic wavelength in the range of about 300 to 320 nm.

40. The apparatus of claim 34, wherein said light irradiating said sample comprises a wavelength of about 310 nm.

41. The apparatus of claim 34, wherein said radiation monitored by said detector comprises a wavelength of about 200 to 900 nm.

42. The apparatus of claim 34, wherein said radiation monitored by said detector comprises a wavelength of about 310 to 600 nm.

43. The apparatus of claim 34, wherein said radiation monitored by said detector comprises a wavelength of about 380 nm and 500 nm.

44. The apparatus of claim 34, further comprising a filter for filtering radiation emitted by said polymer sample.

45. The apparatus of claim 34, wherein the polymer comprises melt polycarbonate.

46. Computer readable media comprising software code for controlling the apparatus of claim 34.

47. An apparatus for the nondestructive monitoring of hydrolytic stability of aromatic polymers, wherein the polymers, when hydrolyzed, create aromatic hydroxyl groups, comprising:

a light source, wherein said light source emits at least one wavelength of substantially monochromatic light to irradiate a polymer sample;

a probe, wherein said probe transmits light from said light source to irradiate a polymer sample, and collects radiation emitted by said polymer sample; and     a detector, wherein said detector monitors radiation emitted by said sample comprising fluorescence which is substantially dependent upon polymer molecular weight, and wherein said light source, probe and detector comprise a portable unit which can be transported to, and used to measure fluorescence from said polymer sample.

48. Computer readable media comprising software code for controlling the apparatus of claim 47.

* * * * *